(12) United States Patent
Francis et al.

(10) Patent No.: US 12,016,772 B2
(45) Date of Patent: Jun. 25, 2024

(54) PROSTHETIC HEART VALVE DEVICES AND ASSOCIATED SYSTEMS AND METHODS

(71) Applicant: Twelve, Inc., Redwood City, CA (US)

(72) Inventors: Richard Francis, Pine Springs, MN (US); Scott Robertson, San Francisco, CA (US); Marian Lally, Galway (IE); Katherine Miyashiro, San Francisco, CA (US); Paraic Frisby, Galway (IE)

(73) Assignee: Twelve, Inc., Redwood City, CA (US)

( * ) Notice: Subject to any disclaimer, the term of this patent is extended or adjusted under 35 U.S.C. 154(b) by 462 days.

(21) Appl. No.: 17/034,422

(22) Filed: Sep. 28, 2020

(65) Prior Publication Data

US 2021/0007844 A1    Jan. 14, 2021

Related U.S. Application Data

(62) Division of application No. 15/643,011, filed on Jul. 6, 2017, now Pat. No. 10,786,352.

(51) Int. Cl.
*A61F 2/24* (2006.01)
*A61B 5/06* (2006.01)

(52) U.S. Cl.
CPC ............ *A61F 2/2418* (2013.01); *A61B 5/068* (2013.01); *A61F 2/2412* (2013.01); *A61F 2/243* (2013.01);
(Continued)

(58) Field of Classification Search
CPC ........ A61F 2/24; A61F 2/2412; A61F 2/2427; A61F 2/2418; A61F 2/95
See application file for complete search history.

(56) References Cited

U.S. PATENT DOCUMENTS

| 3,526,219 A | 9/1970 | Balamuth |
| 3,565,062 A | 2/1971 | Kuris |

(Continued)

FOREIGN PATENT DOCUMENTS

| CN | 1440261 A | 9/2003 |
| CN | 101076290 A | 11/2007 |

(Continued)

OTHER PUBLICATIONS

US 9,265,606 B2, 02/2016, Buchbinder et al. (withdrawn)
(Continued)

*Primary Examiner* — Diane D Yabut
*Assistant Examiner* — Christina C Lauer
(74) *Attorney, Agent, or Firm* — Medler Ferro Woodhouse & Mills PLLC

(57) ABSTRACT

The present technology is a prosthetic heart valve device, and related systems and methods, for treating a native valve of a human heart having a native annulus and native leaflets. One embodiment comprises a valve support, a prosthetic valve assembly within the valve support, and an anchoring member. The device further includes an extension member coupled to the anchoring member and having an annular first portion coupled to the anchoring member and a second portion coupled to the first portion. The extension member is folded in a delivery configuration such that the first portion overlaps the second portion. When released from the a delivery catheter, the extension member unfolds such that the first portion extends radially outwardly from the anchoring member and the second portion extends radially outwardly from the first portion.

11 Claims, 9 Drawing Sheets

(52) U.S. Cl.
CPC ............... *A61F 2210/0014* (2013.01); *A61F 2250/0002* (2013.01); *A61F 2250/0098* (2013.01)

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,739,402 A | 6/1973 | Kahn et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,388,735 A | 6/1983 | Ionescu et al. |
| 4,423,525 A | 1/1984 | Vallana et al. |
| 4,431,006 A | 2/1984 | Trimmer et al. |
| 4,441,216 A | 4/1984 | Ionescu et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,629,459 A | 12/1986 | Ionescu et al. |
| 4,646,736 A | 3/1987 | Auth |
| 4,653,577 A | 3/1987 | Noda |
| 4,666,442 A | 5/1987 | Arru et al. |
| 4,679,556 A | 7/1987 | Lubock et al. |
| 4,692,139 A | 9/1987 | Stiles |
| 4,747,821 A | 5/1988 | Kensey et al. |
| 4,750,902 A | 6/1988 | Wuchinich et al. |
| 4,758,151 A | 7/1988 | Arru et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,892,540 A | 1/1990 | Vallana |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,002,567 A | 3/1991 | Bona et al. |
| 5,058,570 A | 10/1991 | Idemoto et al. |
| 5,069,664 A | 12/1991 | Guess et al. |
| 5,076,276 A | 12/1991 | Sakurai et al. |
| 5,084,151 A | 1/1992 | Vallana et al. |
| 5,104,406 A | 4/1992 | Curcio et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,370,684 A | 12/1994 | Vallana et al. |
| 5,387,247 A | 2/1995 | Vallana et al. |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,713,953 A | 2/1998 | Vallana et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,873,812 A | 2/1999 | Ciana et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,287,339 B1 * | 9/2001 | Vazquez ............ A61F 2/2409 623/2.11 |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,693,859 B1 | 2/2004 | Kulakowski et al. |
| 6,693,862 B1 | 2/2004 | Shigemori |
| 6,694,121 B2 | 2/2004 | Seki |
| 6,702,748 B1 | 3/2004 | Nita et al. |
| 6,730,121 B2 | 5/2004 | Ortiz et al. |
| 6,746,463 B1 | 6/2004 | Schwartz |
| 6,774,278 B1 | 8/2004 | Ragheb et al. |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |

(56) References Cited

U.S. PATENT DOCUMENTS

| | | |
|---|---|---|
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,220,277 B2 | 5/2007 | Arru et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,574 B2 | 3/2009 | Le et al. |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 7,993,392 B2 | 8/2011 | Righini et al. |
| 8,002,826 B2 | 8/2011 | Seguin |
| 8,006,535 B2 | 8/2011 | Righini et al. |
| 8,052,750 B2 | 11/2011 | Tuval et al. |
| 8,057,539 B2 | 11/2011 | Ghione et al. |
| 8,062,355 B2 | 11/2011 | Figulla et al. |
| 8,070,799 B2 | 12/2011 | Righini et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,353,953 B2 | 1/2013 | Giannetti et al. |
| 8,398,704 B2 | 3/2013 | Straubinger et al. |
| 8,403,981 B2 | 3/2013 | Forster et al. |
| 8,403,982 B2 | 3/2013 | Giannetti et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,486,137 B2 | 6/2013 | Suri et al. |
| 8,475,521 B2 | 7/2013 | Suri et al. |
| 8,496,671 B1 | 7/2013 | Hausen |
| 8,512,252 B2 | 8/2013 | Ludomirsky et al. |
| 8,512,397 B2 | 8/2013 | Rolando et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,539,662 B2 | 9/2013 | Stacchino et al. |
| 8,540,767 B2 | 9/2013 | Zhang |
| 8,540,768 B2 | 9/2013 | Stacchino et al. |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,640,521 B2 | 2/2014 | Righini et al. |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,715,207 B2 | 5/2014 | Righini et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,808,367 B2 | 8/2014 | Suri et al. |
| 8,812,431 B2 | 8/2014 | Voigt et al. |
| 8,828,043 B2 | 9/2014 | Chambers |
| 8,834,563 B2 | 9/2014 | Righini |
| 8,840,661 B2 | 9/2014 | Manasse |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,920,492 B2 | 12/2014 | Stacchino et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,329 B2 | 3/2015 | Seguin et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,056,008 B2 | 6/2015 | Righini et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,114,010 B2 | 8/2015 | Gaschino et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,138,314 B2 | 9/2015 | Rolando et al. |
| 9,149,207 B2 | 10/2015 | Sauter et al. |
| 9,161,836 B2 | 10/2015 | Rolando et al. |
| 9,180,005 B1 | 11/2015 | Lashinski et al. |
| 9,186,249 B2 | 11/2015 | Rolando et al. |
| 9,192,466 B2 | 11/2015 | Kovalsky et al. |
| 9,192,471 B2 | 11/2015 | Bolling |

(56) References Cited

U.S. PATENT DOCUMENTS

| | | |
|---|---|---|
| 9,204,819 B2 | 12/2015 | Grunwald et al. |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,248,017 B2 | 2/2016 | Rolando et al. |
| 9,254,192 B2 | 2/2016 | Lutter et al. |
| 9,271,833 B2 | 3/2016 | Kim et al. |
| 9,289,289 B2 | 3/2016 | Rolando et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,207 B2 | 5/2016 | Grunwald et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,105 B2 | 6/2016 | Marchisio et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,421,094 B2 | 8/2016 | Schweich, Jr. et al. |
| 9,433,574 B2 | 9/2016 | Martin et al. |
| 9,480,559 B2 | 11/2016 | Vidlund et al. |
| 9,486,313 B2 | 11/2016 | Stacchino et al. |
| 9,504,835 B2 | 11/2016 | Graindorge |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,700,409 B2 | 7/2017 | Braido et al. |
| 9,700,411 B2 | 7/2017 | Klima et al. |
| 9,700,413 B2 | 7/2017 | Ruyra Baliarda et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,788,931 B2 | 10/2017 | Giordano et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Colemam |
| 9,848,981 B2 | 12/2017 | Suri et al. |
| 9,848,983 B2 | 12/2017 | Lashinski et al. |
| 9,861,477 B2 | 1/2018 | Backrus et al. |
| 9,861,480 B2 | 1/2018 | Zakai et al. |
| 9,867,695 B2 | 1/2018 | Stacchino et al. |
| 9,895,223 B2 | 2/2018 | Stacchino et al. |
| 9,895,225 B2 | 2/2018 | Rolando et al. |
| 9,918,841 B2 | 3/2018 | Righini et al. |
| 9,974,647 B2 | 5/2018 | Ganesan et al. |
| 10,058,313 B2 | 8/2018 | Manasse |
| 10,065,032 B2 | 9/2018 | Ollivier |
| 10,098,733 B2 | 10/2018 | Righini |
| 10,117,741 B2 | 11/2018 | Schweich, Jr. et al. |
| 10,143,550 B2 | 12/2018 | Achiluzzi |
| 10,213,301 B2 | 2/2019 | Ganesan et al. |
| 10,245,141 B2 | 4/2019 | Ghione et al. |
| 10,265,166 B2 | 4/2019 | Schweich, Jr. et al. |
| 10,285,810 B2 | 5/2019 | Schweich, Jr. et al. |
| 10,449,039 B2 | 10/2019 | Ganesan et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2002/0188350 A1 | 12/2002 | Arru et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0228477 A1 | 10/2005 | Grainger et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spencer et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0142906 A1* | 6/2007 | Figulla ................. A61F 2/2436 623/1.36 |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0147181 A1 | 6/2008 | Ghione et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0241218 A1 | 10/2008 | McMorrow et al. |
| 2008/0243245 A1 | 10/2008 | Thambar et al. |
| 2008/0243246 A1 | 10/2008 | Ryan et al. |
| 2008/0262603 A1 | 10/2008 | Giaquinta et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0105794 A1 | 4/2009 | Ziamo et al. |
| 2009/0157174 A1 | 6/2009 | Yoganathan et al. |

(56) References Cited

U.S. PATENT DOCUMENTS

| | | |
|---|---|---|
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023115 A1 | 1/2010 | Robaina et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076376 A1 | 3/2010 | Manasse et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0071623 A1 | 3/2011 | Finch et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kovalsky et al. |
| 2012/0067103 A1 | 3/2012 | Bienvenu et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2012/0303048 A1 | 11/2012 | Manasse |
| 2013/0123915 A1 | 5/2013 | Giannetti et al. |
| 2013/0166017 A1 | 6/2013 | Cartledge |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0338766 A1 | 12/2013 | Hastings et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |

(56) References Cited

U.S. PATENT DOCUMENTS

| | | |
|---|---|---|
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0207011 A1 | 7/2014 | Righini et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222136 A1 | 8/2014 | Geist et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351904 A1 | 12/2015 | Cooper et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0015543 A1 | 1/2016 | Perouse et al. |
| 2016/0030169 A1 | 2/2016 | Shahriani |
| 2016/0030171 A1 | 2/2016 | Quijano et al. |
| 2016/0038246 A1 | 2/2016 | Wang et al. |
| 2016/0038280 A1* | 2/2016 | Morriss ............... A61F 2/2436 623/2.18 |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |

(56) References Cited

U.S. PATENT DOCUMENTS

| | | | |
|---|---|---|---|
| 2016/0158002 A1 | 6/2016 | Wallace et al. |
| 2016/0158003 A1 | 6/2016 | Wallace et al. |
| 2016/0158415 A1 | 6/2016 | Strasly et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0020666 A1 | 1/2017 | Revuelta et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128203 A1 | 5/2017 | Zhang et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296339 A1 | 10/2017 | Thambar et al. |
| 2017/0319333 A1 | 11/2017 | Tegels et al. |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinksi et al. |
| 2017/0360558 A1 | 12/2017 | Ma |
| 2017/0360585 A1 | 12/2017 | White |
| 2018/0021129 A1 | 1/2018 | Peterson et al. |
| 2018/0161585 A1 | 6/2018 | Ollivier |
| 2018/0214263 A1 | 8/2018 | Rolando et al. |
| 2018/0221147 A1 | 8/2018 | Ganesan et al. |
| 2018/0235753 A1 | 8/2018 | Ganesan et al. |
| 2018/0296335 A1 | 10/2018 | Miyashiro |
| 2018/0338832 A1 | 11/2018 | Ganesan et al. |
| 2019/0000618 A1 | 1/2019 | Schweich, Jr. et al. |
| 2019/0008635 A1 | 1/2019 | Francis et al. |
| 2019/0009363 A1 | 1/2019 | Beck |
| 2019/0029814 A1 | 1/2019 | Schweich, Jr. et al. |
| 2019/0142581 A1 | 5/2019 | Maiso et al. |
| 2019/0183641 A1 | 6/2019 | Ganesan et al. |
| 2019/0192292 A1 | 6/2019 | Schweich, Jr. et al. |

FOREIGN PATENT DOCUMENTS

| | | |
|---|---|---|
| CN | 101291637 A | 10/2008 |
| CN | 103491900 A | 1/2014 |
| DE | 19605042 A1 | 1/1998 |
| DE | 102006052564 B3 | 12/2007 |
| EP | 186104 A2 | 7/1986 |
| EP | 0224080 B1 | 7/1992 |
| EP | 1512383 A2 | 3/2005 |
| EP | 1088529 B1 | 6/2005 |
| EP | 1545371 A2 | 6/2005 |
| EP | 1551274 A2 | 7/2005 |
| EP | 1629794 A2 | 3/2006 |
| EP | 1646332 A2 | 4/2006 |
| EP | 1702247 A2 | 9/2006 |
| EP | 1734903 A1 | 12/2006 |
| EP | 1891914 | 2/2008 |
| EP | 1967164 A2 | 9/2008 |
| EP | 2026280 A1 | 2/2009 |
| EP | 2033581 A1 | 3/2009 |
| EP | 2037829 A2 | 3/2009 |
| EP | 2081519 A2 | 7/2009 |
| EP | 2111190 A2 | 10/2009 |
| EP | 2142143 A2 | 1/2010 |
| EP | 2167742 A1 | 3/2010 |
| EP | 2014257 B1 | 9/2010 |
| EP | 2278944 A2 | 2/2011 |
| EP | 2033597 B1 | 3/2011 |
| EP | 2306821 A1 | 4/2011 |
| EP | 2327429 A1 | 6/2011 |
| EP | 2165651 B1 | 8/2011 |
| EP | 1719476 B1 | 11/2011 |
| EP | 2399527 A1 | 12/2011 |
| EP | 2400924 | 1/2012 |
| EP | 2400926 A2 | 1/2012 |
| EP | 2410947 A1 | 2/2012 |
| EP | 2416739 A2 | 2/2012 |
| EP | 2419050 | 2/2012 |
| EP | 2399527 A8 | 3/2012 |
| EP | 2444031 A2 | 4/2012 |
| EP | 2488126 A1 | 8/2012 |
| EP | 2509538 A2 | 10/2012 |
| EP | 2549955 A1 | 1/2013 |
| EP | 2549956 A1 | 1/2013 |
| EP | 2566416 A1 | 3/2013 |
| EP | 2586492 A1 | 5/2013 |
| EP | 2618784 A2 | 7/2013 |
| EP | 2623068 A1 | 8/2013 |
| EP | 2626013 A2 | 8/2013 |
| EP | 2629699 A1 | 8/2013 |
| EP | 2633457 A1 | 9/2013 |
| EP | 2637659 A1 | 9/2013 |
| EP | 2641569 A1 | 9/2013 |
| EP | 2644158 | 10/2013 |
| EP | 2654624 A1 | 10/2013 |
| EP | 2656794 A1 | 10/2013 |
| EP | 2656795 A1 | 10/2013 |
| EP | 2656796 A1 | 10/2013 |
| EP | 2667823 A1 | 12/2013 |
| EP | 2670358 A2 | 12/2013 |
| EP | 2676640 A1 | 12/2013 |
| EP | 2688041 A2 | 1/2014 |
| EP | 2695586 | 2/2014 |
| EP | 2697721 A2 | 2/2014 |
| EP | 2713953 A1 | 4/2014 |
| EP | 2714068 A2 | 4/2014 |
| EP | 2723272 A2 | 4/2014 |
| EP | 2723273 A2 | 4/2014 |
| EP | 2723277 A1 | 4/2014 |
| EP | 2739214 A2 | 6/2014 |
| EP | 2741711 A2 | 6/2014 |
| EP | 2750630 A1 | 7/2014 |
| EP | 2750631 A1 | 7/2014 |
| EP | 2755562 A1 | 7/2014 |
| EP | 2755602 A1 | 7/2014 |
| EP | 2757962 A1 | 7/2014 |
| EP | 2777616 A1 | 9/2014 |
| EP | 2777617 A1 | 9/2014 |
| EP | 2782523 A1 | 10/2014 |
| EP | 2785282 A1 | 10/2014 |
| EP | 2786817 | 10/2014 |
| EP | 2790609 A1 | 10/2014 |
| EP | 2793751 A1 | 10/2014 |
| EP | 2229921 B1 | 11/2014 |
| EP | 2809263 A2 | 12/2014 |
| EP | 2810620 A1 | 12/2014 |
| EP | 2814428 A1 | 12/2014 |

(56) References Cited

FOREIGN PATENT DOCUMENTS

| | | |
|---|---|---|
| EP | 2814429 A1 | 12/2014 |
| EP | 2819617 A1 | 1/2015 |
| EP | 2819618 A1 | 1/2015 |
| EP | 2819619 A1 | 1/2015 |
| EP | 2833836 A1 | 2/2015 |
| EP | 2838475 A1 | 2/2015 |
| EP | 2839815 | 2/2015 |
| EP | 2844190 | 3/2015 |
| EP | 2849680 A2 | 3/2015 |
| EP | 2849681 A1 | 3/2015 |
| EP | 2852354 A2 | 4/2015 |
| EP | 2861186 A2 | 4/2015 |
| EP | 2870933 | 5/2015 |
| EP | 2873011 A1 | 5/2015 |
| EP | 2875797 A1 | 5/2015 |
| EP | 2760375 | 6/2015 |
| EP | 2882374 A1 | 6/2015 |
| EP | 2886082 | 6/2015 |
| EP | 2886083 A1 | 6/2015 |
| EP | 2886084 A1 | 6/2015 |
| EP | 2895111 A2 | 7/2015 |
| EP | 2250976 B1 | 8/2015 |
| EP | 2901966 A1 | 8/2015 |
| EP | 2907479 A1 | 8/2015 |
| EP | 2945572 A1 | 11/2015 |
| EP | 2948094 A1 | 12/2015 |
| EP | 2948102 A1 | 12/2015 |
| EP | 2964152 A1 | 1/2016 |
| EP | 2967859 A1 | 1/2016 |
| EP | 2967860 A1 | 1/2016 |
| EP | 2967866 A2 | 1/2016 |
| EP | 2968847 A1 | 1/2016 |
| EP | 2981208 | 2/2016 |
| EP | 2982336 A1 | 2/2016 |
| EP | 2999433 A1 | 3/2016 |
| EP | 3003187 A1 | 4/2016 |
| EP | 3003219 A1 | 4/2016 |
| EP | 3003220 A1 | 4/2016 |
| EP | 3010447 A1 | 4/2016 |
| EP | 3013281 A1 | 5/2016 |
| EP | 3017792 A1 | 5/2016 |
| EP | 3021792 A2 | 5/2016 |
| EP | 3023117 A1 | 5/2016 |
| EP | 3027143 A1 | 6/2016 |
| EP | 3033048 A2 | 6/2016 |
| EP | 3037064 A1 | 6/2016 |
| EP | 3050541 A1 | 8/2016 |
| EP | 3079633 | 10/2016 |
| EP | 3229736 | 11/2016 |
| EP | 3102152 | 12/2016 |
| EP | 2470119 B1 | 5/2017 |
| EP | 2999436 A4 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256077 | 12/2017 |
| EP | 3258883 | 12/2017 |
| EP | 3273910 | 1/2018 |
| JP | 6504516 | 5/1994 |
| JP | H10258124 A | 9/1998 |
| JP | 2002509756 A | 4/2002 |
| JP | 2005280917 A | 10/2005 |
| JP | 2008528117 A | 7/2008 |
| JP | 2008541863 A | 11/2008 |
| JP | 2009195712 A | 9/2009 |
| JP | 2010-519957 A | 6/2010 |
| JP | 2010518947 A | 6/2010 |
| JP | 2013-509961 A | 3/2013 |
| JP | 5219518 B2 | 6/2013 |
| JP | 2015-510415 A | 4/2015 |
| JP | 2015-516822 A | 6/2015 |
| JP | 2016-506795 A | 3/2016 |
| JP | 2016-512753 A | 5/2016 |
| WO | WO-1992017118 A1 | 10/1992 |
| WO | WO-1995016407 A1 | 6/1995 |
| WO | WO-1999004730 A1 | 2/1999 |
| WO | WO-1999039648 A1 | 8/1999 |
| WO | WO-1999049799 A1 | 10/1999 |
| WO | WO-2001010343 | 2/2001 |
| WO | WO-2002003892 A1 | 1/2002 |
| WO | WO-2002028421 A1 | 4/2002 |
| WO | WO-2002039908 A2 | 5/2002 |
| WO | WO-2003043685 A2 | 5/2003 |
| WO | WO-2004084746 A2 | 10/2004 |
| WO | WO-2004093728 A2 | 11/2004 |
| WO | WO-2004096097 A2 | 11/2004 |
| WO | WO-2004112657 A1 | 12/2004 |
| WO | WO-2005002466 A2 | 1/2005 |
| WO | WO-2005007219 A2 | 1/2005 |
| WO | WO-2005009285 A2 | 2/2005 |
| WO | WO-2005009506 A2 | 2/2005 |
| WO | WO-2005087140 A1 | 9/2005 |
| WO | WO-2006041877 A2 | 4/2006 |
| WO | WO-2006063199 A2 | 6/2006 |
| WO | WO-2007008371 A2 | 1/2007 |
| WO | WO-2007067820 A2 | 6/2007 |
| WO | WO-2008022077 A2 | 2/2008 |
| WO | WO-2008028569 A1 | 3/2008 |
| WO | WO-2008035337 A2 | 3/2008 |
| WO | WO-2008103497 A2 | 8/2008 |
| WO | WO-2008103722 | 8/2008 |
| WO | 2008/106223 A1 | 9/2008 |
| WO | WO-2008129405 A2 | 10/2008 |
| WO | WO-2009045338 A2 | 4/2009 |
| WO | WO-2009091509 | 7/2009 |
| WO | WO-2010006627 A1 | 1/2010 |
| WO | WO-2010008549 A1 | 1/2010 |
| WO | WO-2010057262 A1 | 5/2010 |
| WO | WO-2010080594 A2 | 7/2010 |
| WO | WO-2010098857 A1 | 9/2010 |
| WO | WO-2010099032 A2 | 9/2010 |
| WO | WO-2010117680 A1 | 10/2010 |
| WO | WO-2010121076 | 10/2010 |
| WO | WO-2011025981 | 3/2011 |
| WO | WO-2011047168 A1 | 4/2011 |
| WO | WO-2011051043 A1 | 5/2011 |
| WO | WO-2011057087 A1 | 5/2011 |
| WO | WO-2011072084 A2 | 6/2011 |
| WO | WO-2011106137 A1 | 9/2011 |
| WO | WO-2011106544 A1 | 9/2011 |
| WO | WO-2011111047 A2 | 9/2011 |
| WO | WO-2011137531 A1 | 11/2011 |
| WO | WO-2011139747 A1 | 11/2011 |
| WO | WO-2012011018 A1 | 1/2012 |
| WO | WO-2012011108 A2 | 1/2012 |
| WO | WO-2012027487 A2 | 3/2012 |
| WO | WO-2012035279 A1 | 3/2012 |
| WO | WO-2012040655 A2 | 3/2012 |
| WO | WO-2012047644 A2 | 4/2012 |
| WO | WO-2012052718 | 4/2012 |
| WO | WO-2012055498 A1 | 5/2012 |
| WO | WO-2012087842 A1 | 6/2012 |
| WO | WO-2012095455 A2 | 7/2012 |
| WO | WO-2012102928 A1 | 8/2012 |
| WO | WO-2012106602 A2 | 8/2012 |
| WO | WO-2012118508 A1 | 9/2012 |
| WO | WO-2012118816 A1 | 9/2012 |
| WO | WO-2012118894 A2 | 9/2012 |
| WO | WO-2012177942 A2 | 12/2012 |
| WO | WO-2013021374 A2 | 2/2013 |
| WO | WO-2013021375 A2 | 2/2013 |
| WO | WO-2013028387 A2 | 2/2013 |
| WO | WO-2013059743 A1 | 4/2013 |
| WO | WO-2013059747 A1 | 4/2013 |

(56) References Cited

FOREIGN PATENT DOCUMENTS

| | | |
|---|---|---|
| WO | 2013/112617 A1 | 8/2013 |
| WO | 2013/126529 A2 | 8/2013 |
| WO | WO-2013114214 A2 | 8/2013 |
| WO | WO-2013120181 A1 | 8/2013 |
| WO | WO-2013123059 A1 | 8/2013 |
| WO | WO-2013128432 A1 | 9/2013 |
| WO | WO-2013130641 A1 | 9/2013 |
| WO | WO-2013131925 A1 | 9/2013 |
| WO | WO-2013140318 A1 | 9/2013 |
| WO | WO-2013148017 A1 | 10/2013 |
| WO | WO-2013148018 A1 | 10/2013 |
| WO | WO-2013148019 A1 | 10/2013 |
| WO | WO-2013150512 A1 | 10/2013 |
| WO | WO-2013152161 A1 | 10/2013 |
| WO | WO-2013158613 A1 | 10/2013 |
| WO | WO-2013169448 A1 | 11/2013 |
| WO | WO-2013175468 A2 | 11/2013 |
| WO | WO-2013176583 A2 | 11/2013 |
| WO | WO-2013188077 A1 | 12/2013 |
| WO | WO-2013192107 A1 | 12/2013 |
| WO | WO-2014036113 A1 | 3/2014 |
| WO | WO-2014043527 A2 | 3/2014 |
| WO | WO-2014047111 A1 | 3/2014 |
| WO | WO-2014047325 A1 | 3/2014 |
| WO | WO-2014055981 A1 | 4/2014 |
| WO | WO-2014059432 A2 | 4/2014 |
| WO | WO-2014064694 A2 | 5/2014 |
| WO | WO-2014066365 A1 | 5/2014 |
| WO | WO-2014089424 A1 | 6/2014 |
| WO | WO-2014093861 A1 | 6/2014 |
| WO | WO-2014111918 A1 | 7/2014 |
| WO | WO-2014114794 A2 | 7/2014 |
| WO | WO-2014114795 A1 | 7/2014 |
| WO | WO-2014114796 A1 | 7/2014 |
| WO | WO-2014114798 A1 | 7/2014 |
| WO | WO-2014116502 A1 | 7/2014 |
| WO | WO-2014121280 A2 | 8/2014 |
| WO | WO-2014128705 A1 | 8/2014 |
| WO | WO-2014134277 A1 | 9/2014 |
| WO | WO-2014138194 A1 | 9/2014 |
| WO | WO-2014138284 A1 | 9/2014 |
| WO | WO-2014138482 A1 | 9/2014 |
| WO | WO-2014138868 A1 | 9/2014 |
| WO | WO-2014144100 A2 | 9/2014 |
| WO | WO-2014144937 A2 | 9/2014 |
| WO | WO-2014145338 A1 | 9/2014 |
| WO | WO-2014147336 A1 | 9/2014 |
| WO | WO-2014152306 A1 | 9/2014 |
| WO | WO-2014152375 A2 | 9/2014 |
| WO | WO-2014152503 A1 | 9/2014 |
| WO | WO-2014153544 A1 | 9/2014 |
| WO | WO-2014158617 A1 | 10/2014 |
| WO | WO-2014162181 A2 | 10/2014 |
| WO | WO-2014162306 A2 | 10/2014 |
| WO | WO-2014163705 A1 | 10/2014 |
| WO | WO-2014168655 A1 | 10/2014 |
| WO | WO-2014179391 A2 | 11/2014 |
| WO | WO-2014181336 A1 | 11/2014 |
| WO | WO-2014189974 A1 | 11/2014 |
| WO | WO-2014191994 A1 | 12/2014 |
| WO | WO-2014194178 A1 | 12/2014 |
| WO | WO-2014201384 A1 | 12/2014 |
| WO | WO-2014201452 A1 | 12/2014 |
| WO | WO-2014205064 A1 | 12/2014 |
| WO | WO-2014207699 A1 | 12/2014 |
| WO | WO-2014210124 A1 | 12/2014 |
| WO | WO-2014210299 A1 | 12/2014 |
| WO | WO-2015009503 A2 | 1/2015 |
| WO | WO-2015020971 A1 | 2/2015 |
| WO | WO-2015028986 A1 | 3/2015 |
| WO | WO-2015051430 A1 | 4/2015 |
| WO | WO-2015052663 A1 | 4/2015 |
| WO | WO-2015057407 A1 | 4/2015 |
| WO | WO-2015057735 A1 | 4/2015 |
| WO | WO-2015057995 A2 | 4/2015 |
| WO | WO-2015061378 A1 | 4/2015 |
| WO | WO-2015061431 A1 | 4/2015 |
| WO | WO-2015061463 A1 | 4/2015 |
| WO | WO-2015061533 A1 | 4/2015 |
| WO | WO-2015075128 A1 | 5/2015 |
| WO | WO-2015081775 A1 | 6/2015 |
| WO | WO-2015089334 A1 | 6/2015 |
| WO | WO-2015092554 A2 | 6/2015 |
| WO | WO-2015118464 A1 | 8/2015 |
| WO | WO-2015120122 A2 | 8/2015 |
| WO | WO-2015125024 A2 | 8/2015 |
| WO | WO-2015127264 A1 | 8/2015 |
| WO | WO-2015127283 A1 | 8/2015 |
| WO | WO-2015128739 A2 | 9/2015 |
| WO | WO-2015128741 A2 | 9/2015 |
| WO | WO-2015128747 A2 | 9/2015 |
| WO | WO-2015132667 A1 | 9/2015 |
| WO | WO-2015132668 A1 | 9/2015 |
| WO | WO-2015135050 A1 | 9/2015 |
| WO | WO-2015142648 A1 | 9/2015 |
| WO | WO-2015142834 A1 | 9/2015 |
| WO | WO-2015148241 A1 | 10/2015 |
| WO | WO-2015171190 A1 | 11/2015 |
| WO | WO-2015171743 A2 | 11/2015 |
| WO | WO-2015179181 | 11/2015 |
| WO | WO-2015191604 | 12/2015 |
| WO | WO-2015191839 A1 | 12/2015 |
| WO | WO-2015195823 A1 | 12/2015 |
| WO | WO-2016011185 A1 | 1/2016 |
| WO | WO-2016020918 A1 | 2/2016 |
| WO | WO-2016027272 A1 | 2/2016 |
| WO | WO-2016059533 A1 | 4/2016 |
| WO | WO-2016065158 A1 | 4/2016 |
| WO | WO-2016073741 A1 | 5/2016 |
| WO | WO-2016083551 A1 | 6/2016 |
| WO | WO-2016093877 A1 | 6/2016 |
| WO | WO-2016097337 A1 | 6/2016 |
| WO | WO-2016108181 A1 | 7/2016 |
| WO | WO-2016133950 | 8/2016 |
| WO | WO-2016150806 | 9/2016 |
| WO | WO-2016201024 | 12/2016 |
| WO | WO-2016209970 | 12/2016 |
| WO | WO-2017011697 | 1/2017 |
| WO | WO-2017062640 | 4/2017 |
| WO | WO-2017096157 | 6/2017 |
| WO | WO-2017100927 | 6/2017 |
| WO | WO-2017101232 | 6/2017 |
| WO | WO-2017117388 | 7/2017 |
| WO | WO-2017127939 | 8/2017 |
| WO | WO-2017136596 | 8/2017 |
| WO | WO-2017173331 | 10/2017 |
| WO | WO-2017196511 | 11/2017 |
| WO | WO-2017196909 | 11/2017 |
| WO | WO-2017196977 | 11/2017 |
| WO | WO-2017197064 | 11/2017 |
| WO | WO-2017218671 | 12/2017 |
| WO | WO-2018017886 | 1/2018 |
| WO | WO-2018029680 | 2/2018 |
| WO | WO-2018167536 | 9/2018 |
| WO | WO-2019069145 | 4/2019 |
| WO | WO-2019209927 | 10/2019 |

OTHER PUBLICATIONS

Notice of Reasons for Rejection, JP Application No. 2019-572483, dated Jun. 27, 2022.
Notice of Reasons for Rejection, JP Application No. 2019-572460, dated Jun. 28, 2022.
Bernard et al., "Aortic Valve Area Evolution After Percutaneous Aortic Valvuloplasty," European Heart Journal, Jul. 1990, vol. 11 (2), pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.
Cimino, "Ultrasonic Surgery: Power Quantification and Efficiency Optimization", Aesthetic Surgery Journal, Feb. 2001, pp. 233-241.

(56) References Cited

OTHER PUBLICATIONS

Cowell et al., "A Randomized Trial of Intensive Lipid-Lowering Therapy in Calcific Aortic Stenosis," NEJM, Jun. 2005, vol. 352 (23), pp. 2389-2397.
De Korte et al., "Characterization of Plaque Components and Vulnerability with Intravascular Ultrasound Elastography", Phys. Med. Biol., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Fitzgerald et al., "Intravascular Sonotherapy Decreased Neointimal Hyperplasia After Stent Implantation in Swine", Circulation, Feb. 2001, vol. 103, pp. 1828-1831.
Freeman et al., "Ultrasonic Aortic Valve Decalcification: Serial Doppler Echocardiographic Follow Up", J Am Coll Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr Interv Cardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population Study Based on Autopsies", J Chronic Dis., Jun. 1979, vol. 32 (5), pp. 355-363.
International Search Report and Written Opinion dated Sep. 11, 2018 for PCT Application No. PCT/US2018/038841, 15 pages.
International Search Report and Written Opinion dated Sep. 4, 2018 for PCT Application No. PCT/US2018/027966, 17 pages.
International Search Report and Written Opinion dated Jul. 11, 2018 for PCT Application No. PCT/US2018/027990, 15 pages.
International Search Report and Written Opinion dated Sep. 11, 2018 for PCT Application No. PCT/US2018/038847, 18 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/US2018/035086, 15 pages.
International Search Report and Written Opinion dated Aug. 9, 2018 for PCT Application No. PCT/US2018/035081, 11 pages.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al"Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94 (11), pp. 1396-1402.

Otto et al., "Three-Year Outcome After Balloon Aortic Valvuloplasty. Insights into Prognosis of Valvular Aortic Stenosis", Circulation, Feb. 1994, vol. 89, pp. 642-650.
Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Eur J Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Apr. 19, 2014 PCT Application No. PCT/US2012/061215.
Search Report and Written Opinion dated Apr. 19, 2014 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992, vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al, "Catheter-Based Ultrasound Thrombolysis", Circulation, Mar. 1997, vol. 95 (6), pp. 1411-1416.

* cited by examiner

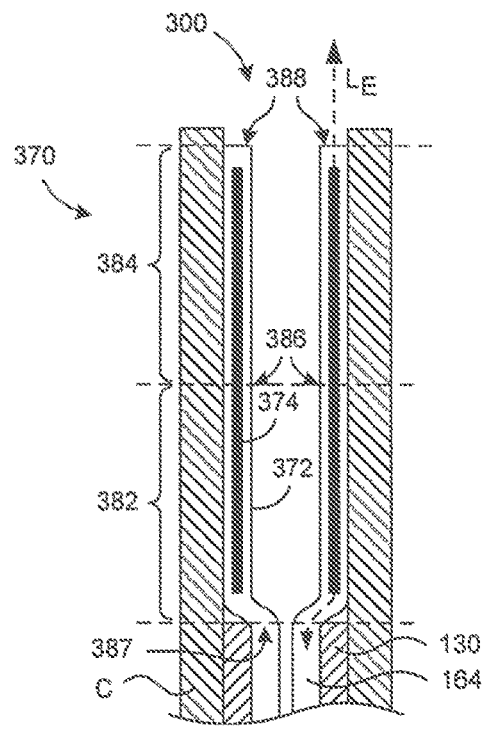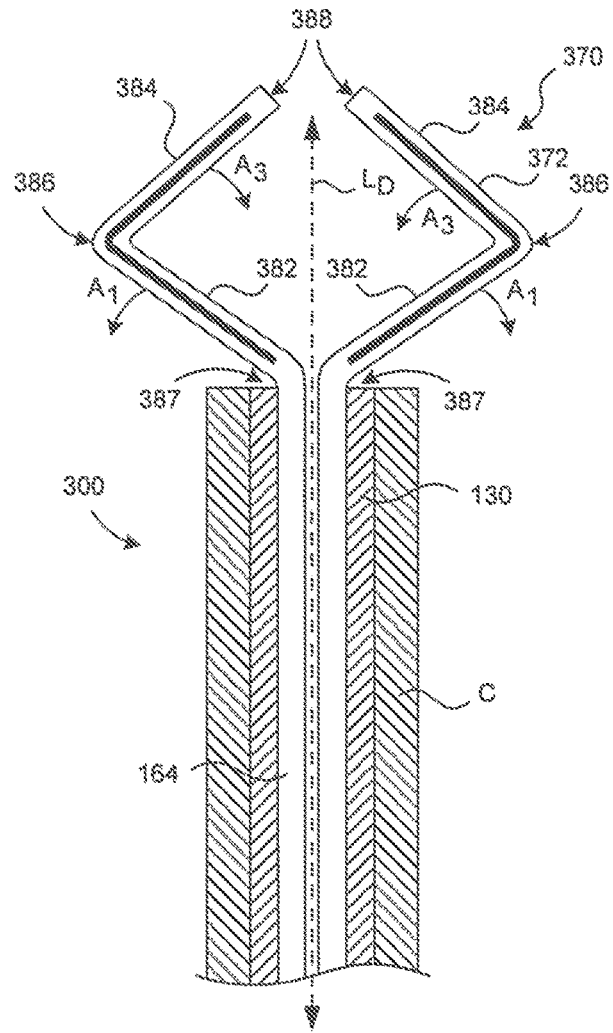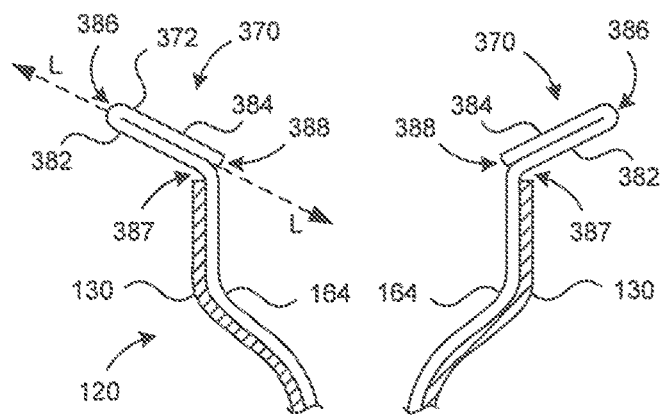
FIG. 9A  FIG. 9B
FIG. 9C

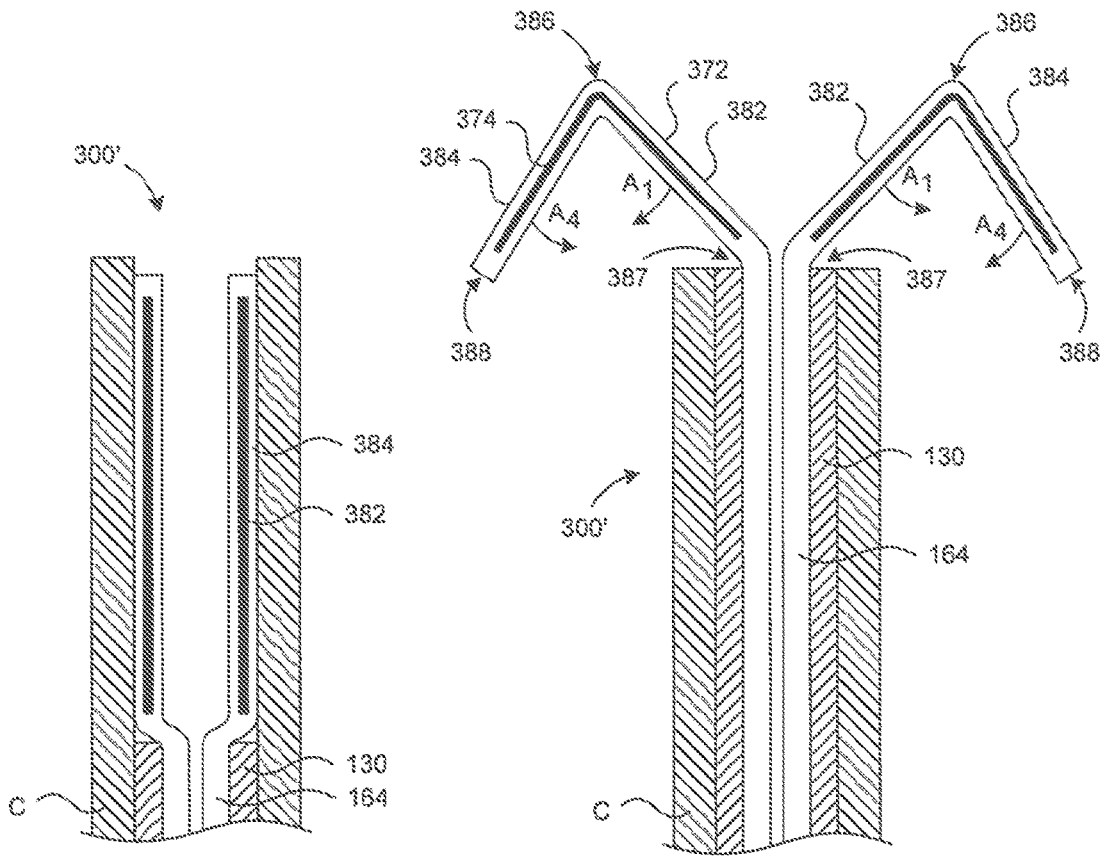
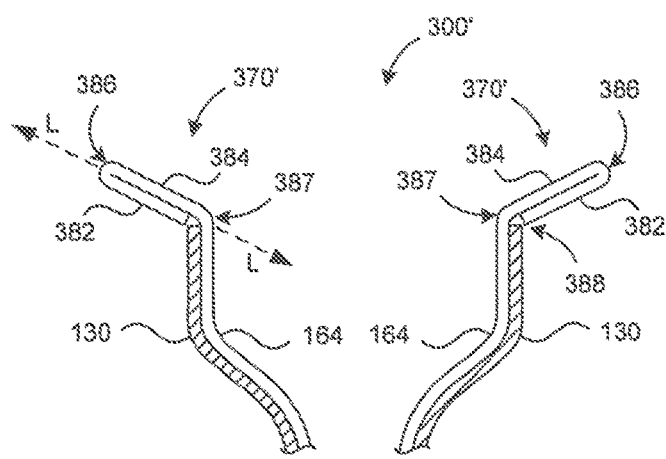
FIG. 10A  FIG. 10B
FIG. 10C

PROSTHETIC HEART VALVE DEVICES AND ASSOCIATED SYSTEMS AND METHODS

CROSS-REFERENCE TO RELATED APPLICATION(S)

The present application is a division of U.S. patent application Ser. No. 15/643,011, filed Jul. 6, 2017, the contents of which are incorporated by reference herein in their entirety. The present application incorporates the subject matter of (1) International Patent Application No. PCT/US2014/029549, filed Mar. 14, 2014, (2) International Patent Application No. PCT/US2012/061219, filed Oct. 19, 2012, (3) International Patent Application No. PCT/US2012/061215, filed Oct. 19, 2012, (4) International Patent Application No. PCT/US2012/043636, filed Jun. 21, 2012. The present application also incorporates the subject matter of U.S. application Ser. No. 15/642,834 U.S. Patent Application Publication No. 2019/0008635), filed Jul. 6, 2017.

TECHNICAL FIELD

The present technology relates generally to prosthetic heart valve devices. In particular, several embodiments are directed to prosthetic mitral valves and devices for percutaneous repair and/or replacement of native mitral valves and associated systems and methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up in to the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, CA, USA) and the Edwards-Sapien® Valve from Edwards Lifesciences (Irvine, CA, USA). Both valve systems include an expandable frame and a tri-leaflet bio-prosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

The triscuspid valve on the right side of the heart, although it normally has three leaflets, poses similar challenges to less invasive treatment as the mitral valve. Therefore there is a need for a better prosthesis to treat tricuspid valve disease as well.

Given the difficulties associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale, and instead emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers and/or letters are used to identify similar or analogous components or features, but the use of the same reference number does not imply that the parts should be construed to be identical. Indeed, in many examples described herein, identically numbered components refer to different embodiments that are distinct in structure and/or function. The headings provided herein are for convenience only.

maintained by the placement of a guide catheter over a guidewire in accordance with various embodiments of the present technology.

Figure 3:
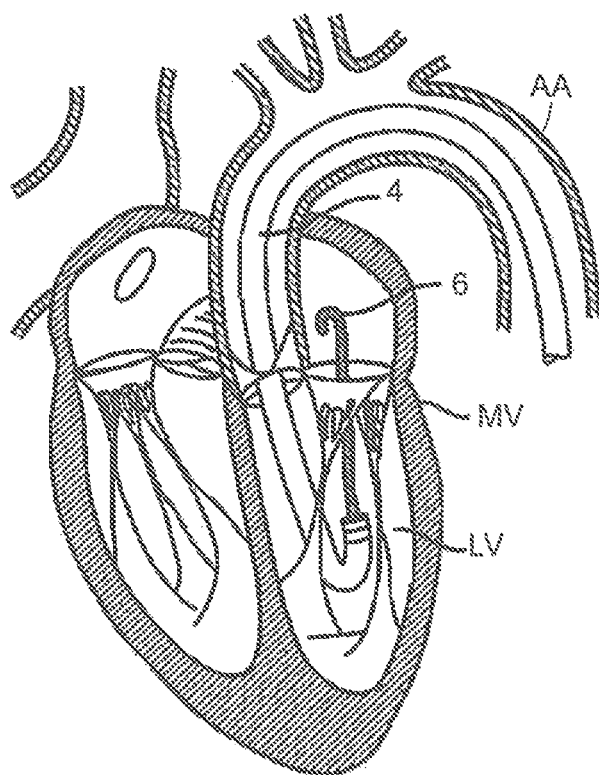
Figure 4:
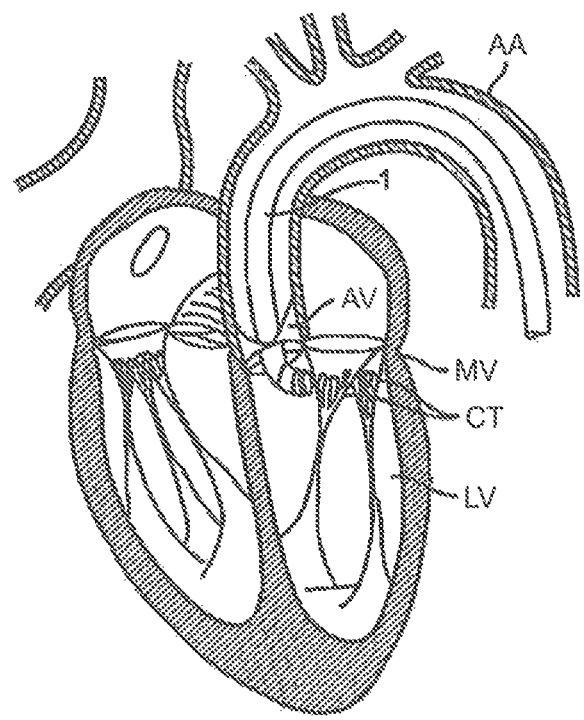

FIGS. 3 and 4 are schematic, cross-sectional illustrations of the heart showing retrograde approaches to the native mitral valve through the aortic valve and arterial vasculature in accordance with various embodiments of the present technology.

Figure 5:
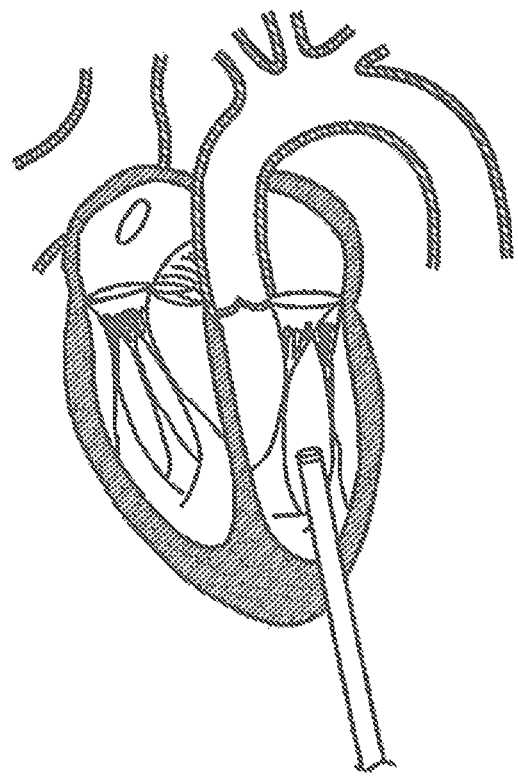

FIG. 5 is a schematic, cross-sectional illustration of the heart showing an approach to the native mitral valve using a trans-apical puncture in accordance with various embodiments of the present technology.

Figure 6A:
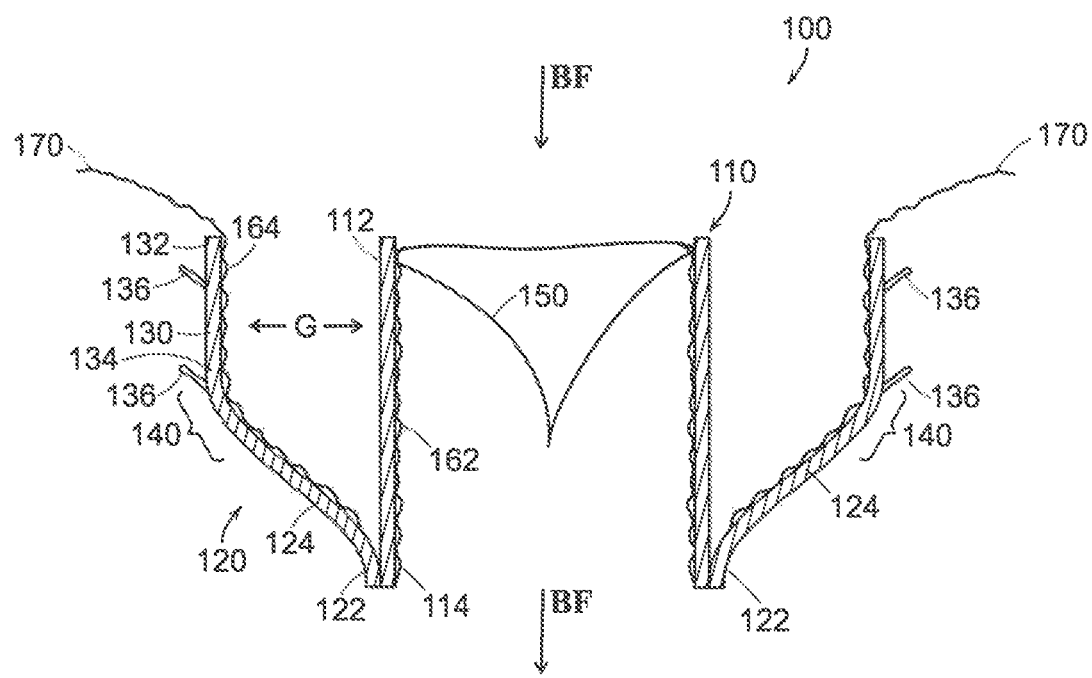
Figure 6B:
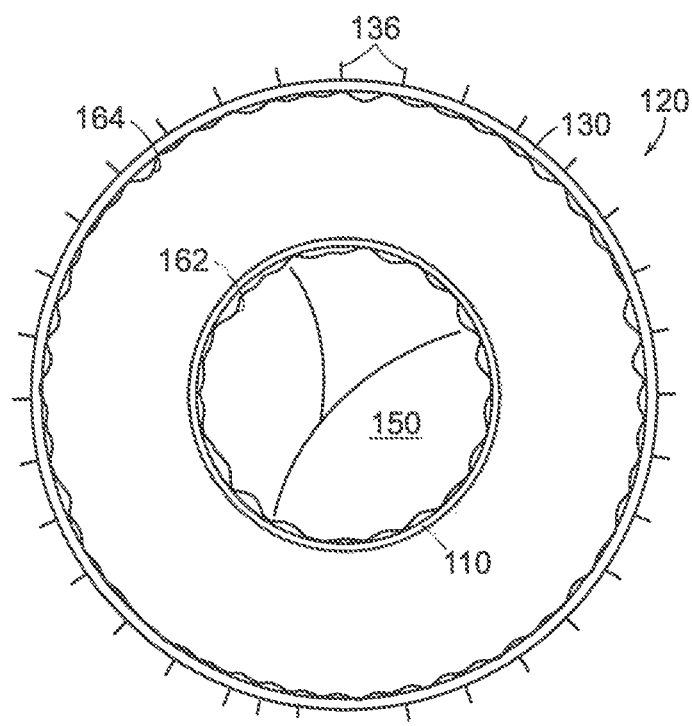

FIG. 6A is a cross-sectional side view and FIG. 6B is a top view schematically illustrating a prosthetic heart valve device in accordance with an embodiment of the present technology.

Figure 7:
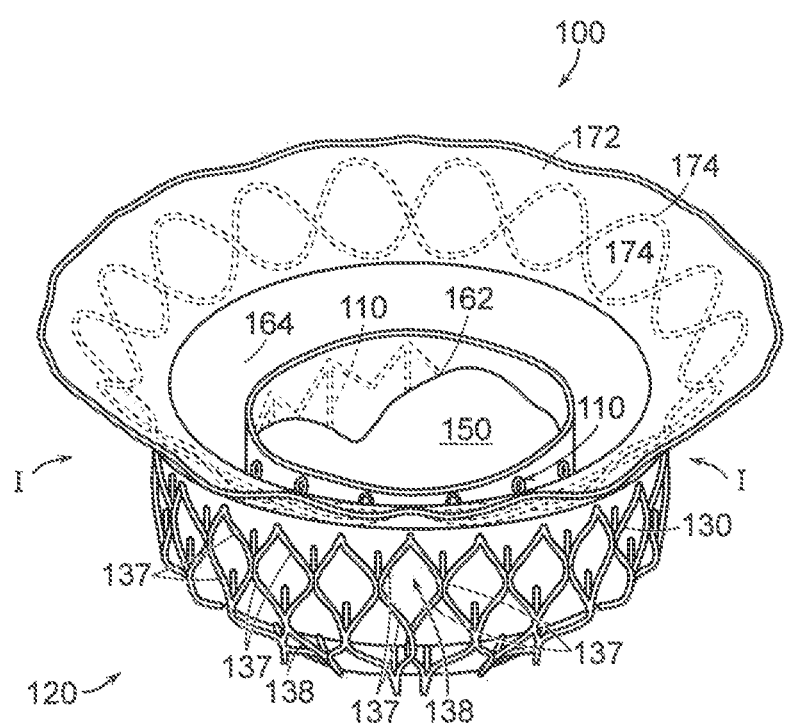

FIG. 7 is a top isometric view of a prosthetic heart valve device in accordance with an embodiment of the present technology, shown in a deployed configuration.

Figure 8A:
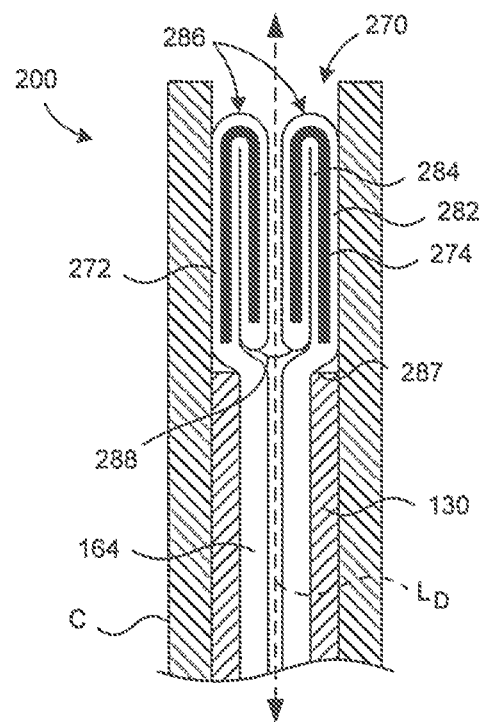

FIG. 8A is a schematic cross-sectional view of a portion of a prosthetic heart valve device in accordance with an embodiment of the present technology, shown in a delivery configuration within a delivery catheter.

Figure 8B:
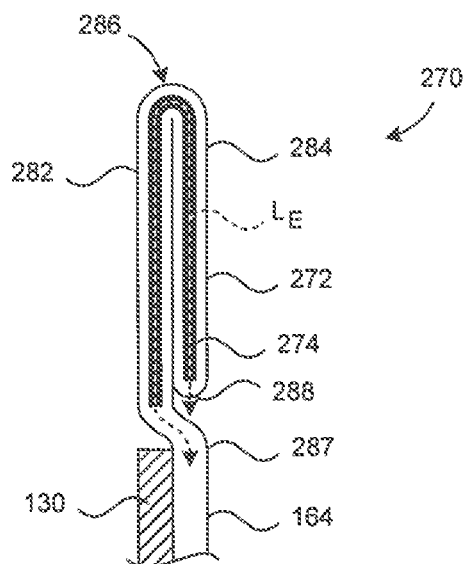

FIG. 8B is an enlarged view of a portion of the extension member shown in FIG. 8A.

Figure 8C:
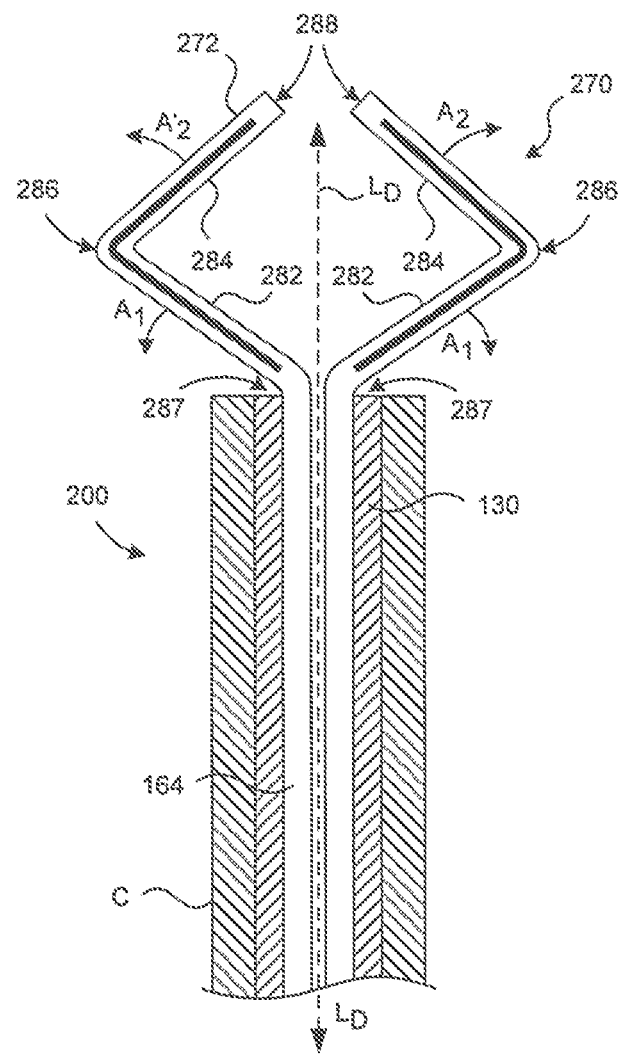

FIG. 8C is a cross-sectional view of the portion of the prosthetic heart valve device of FIG. 8A, shown as the extension member is being released from the distal end of the delivery catheter and transforming from the delivery configuration to a deployed configuration.

Figure 8D:
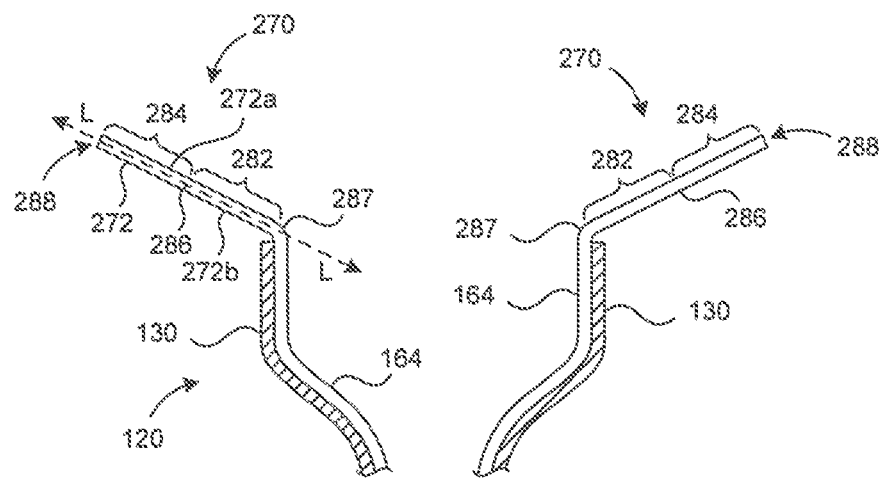

FIG. 8D is a cross-sectional view of the prosthetic heart valve device of FIG. 8A, shown in a deployed configuration.

FIG. 9A is a schematic cross-sectional view of a portion of a prosthetic heart valve device shown in a delivery configuration within a delivery catheter in accordance with an embodiment of the present technology.

FIG. 9B is a cross-sectional view of the portion of the prosthetic heart valve device of FIG. 9A showing the extension member as it releases from the distal end of the delivery catheter and transforms from the delivery configuration to a deployed configuration.

FIG. 9C is a cross-sectional view of the prosthetic heart valve device of FIG. 9A, shown in a deployed configuration.

FIG. 10A is a schematic cross-sectional view of a portion of a prosthetic heart valve device shown in a delivery configuration within a delivery catheter in accordance with an embodiment of the present technology.

FIG. 10B is a cross-sectional view of a portion of a prosthetic heart valve device in accordance with an embodiment of the present technology showing the extension member as it releases from the distal end of the delivery catheter and transforms from the delivery configuration to a deployed configuration.

FIG. 10C is a cross-sectional view of the prosthetic heart valve device of FIG. 10A, shown in a deployed configuration.

DETAILED DESCRIPTION

Specific details of several embodiments of the technology are described below with reference to FIGS. 1-10C. Although many of the embodiments are described below with respect to prosthetic valve devices, systems, and methods for percutaneous replacement of a native mitral valve, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-10C.

With regard to the terms "distal" and "proximal" within this description, unless otherwise specified, the terms can reference a relative position of the portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to mitral valve replacement devices that address the unique challenges of percutaneously replacing native mitral valves and are well-suited for navigating through the heart anatomy to the mitral valve annulus. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

Embodiments of the present technology provide systems, methods and apparatus to treat heart valves of the body, such as the mitral valve, that address the challenges associated with the anatomy of the mitral valve and provide for improved maneuverability of the device when positioned within the delivery catheter. The apparatus and methods enable a percutaneous approach using a catheter delivered intravascularly through a vein or artery into the heart, or through a cannula inserted through the heart wall. For example, the apparatus and methods are particularly well-suited for trans-septal approaches, but can also be trans-apical, trans-atrial, and direct aortic delivery of a prosthetic replacement valve to a target location in the heart. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

Access to the Mitral Valve

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

Figure 1:
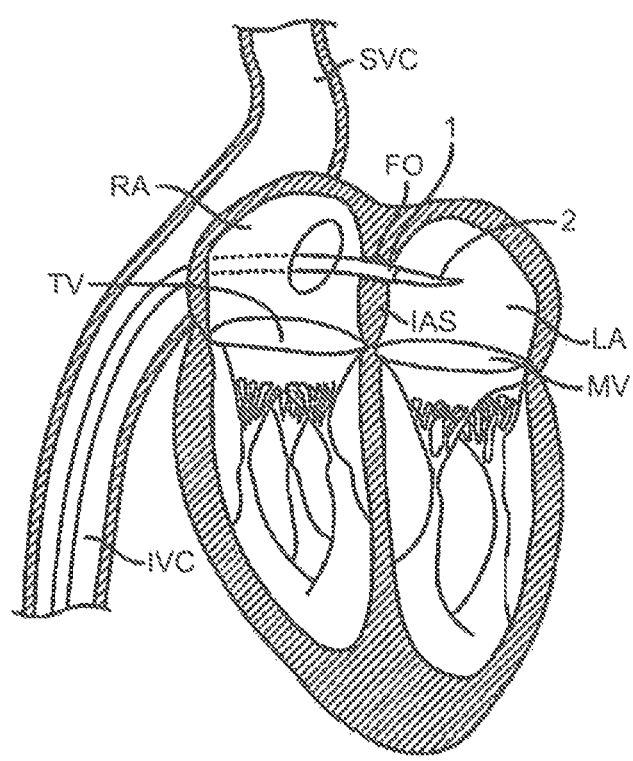
FIG. 1 is a schematic, cross-sectional illustration of the heart showing an antegrade approach to the native mitral valve from the venous vasculature in accordance with various embodiments of the present technology.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
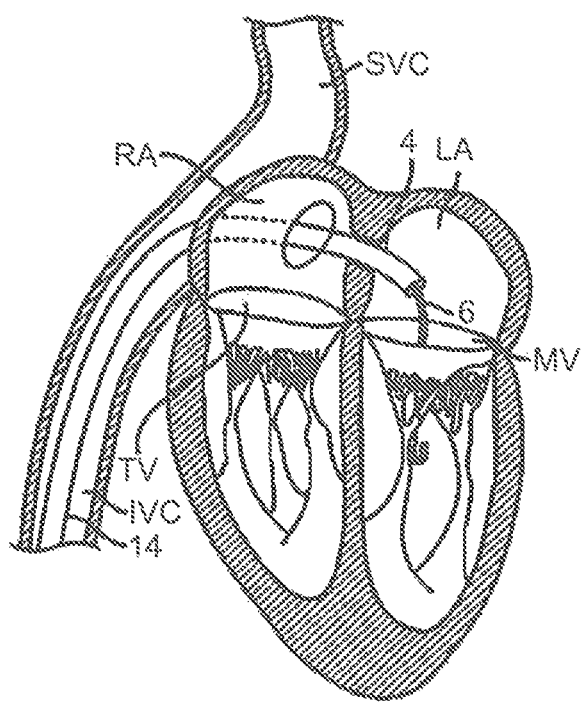
FIG. 2 is a schematic, cross-sectional illustration of the heart showing access through the inter-atrial septum (IAS)

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

FIG. 5 shows a trans-apical approach via a trans-apical puncture. In this approach, access to the heart is via a thoracic incision, which can be a conventional open thoracotomy or sternotomy, or a smaller intercostal or sub-xyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Prosthetic Heart Valve Devices and Methods

Embodiments of the present technology can treat one or more of the valves of the heart, and in particular several embodiments advantageously treat the mitral valve. The prosthetic valve devices of the present technology can also be suitable for replacement of other valves (e.g., a bicuspid or tricuspid valve) in the heart of the patient. Examples of prosthetic heart valve devices in accordance with embodiments of the present technology are described in this section with reference to FIGS. 6A-8B. Specific elements, substructures, advantages, uses, and/or other features of the embodiments described with reference to FIGS. 6A-8B can be suitably interchanged, substituted or otherwise configured with one another. Furthermore, suitable elements of the embodiments described with reference to FIGS. 6A-8B can be used as stand-alone and/or self-contained devices.

FIG. 6A is a side cross-sectional view and FIG. 6B is a top plan view of a prosthetic heart valve device ("device") 100 in accordance with an embodiment of the present technology. The device 100 includes a valve support 110, an anchoring member 120 attached to the valve support 110, and a prosthetic valve assembly 150 within the valve support 110. Referring to FIG. 6A, the valve support 110 has an inflow region 112 and an outflow region 114. The prosthetic valve assembly 150 is arranged within the valve support 110 to allow blood to flow from the inflow region 112 through the outflow region 114 (arrows BF), but prevent blood from flowing in a direction from the outflow region 114 through the inflow region 112.

In the embodiment shown in FIG. 6A, the anchoring member 120 includes a base 122 attached to the outflow region 114 of the valve support 110 and a plurality of arms 124 projecting laterally outward from the base 122. The anchoring member 120 also includes a fixation structure 130 extending from the arms 124. The fixation structure 130 can include a first portion 132 and a second portion 134. The first portion 132 of the fixation structure 130, for example, can be an upstream region of the fixation structure 130 that, in a deployed configuration as shown in FIG. 6A, is spaced laterally outward apart from the inflow region 112 of the valve support 110 by a gap G. The second portion 134 of the fixation structure 130 can be a downstream-most portion of the fixation structure 130. The fixation structure 130 can be a cylindrical ring (e.g., straight cylinder or conical), and the outer surface of the fixation structure 130 can define an annular engagement surface configured to press outwardly against the native annulus. The fixation structure 130 can further include a plurality of fixation elements 136 that project radially outward and are inclined toward an upstream direction. The fixation elements 136, for example, can be barbs, hooks, or other elements that are inclined only in the upstream direction (e.g., a direction extending away from the downstream portion of the device 100).

Referring still to FIG. 6A, the anchoring member 120 has a smooth bend 140 between the arms 124 and the fixation structure 130. For example, the second portion 134 of the fixation structure 130 extends from the arms 124 at the smooth bend 140. The arms 124 and the fixation structure 130 can be formed integrally from a continuous strut or support element such that the smooth bend 140 is a bent portion of the continuous strut. In other embodiments, the smooth bend 140 can be a separate component with respect to either the arms 124 or the fixation structure 130. For example, the smooth bend 140 can be attached to the arms 124 and/or the fixation structure 130 using a weld, adhesive or other technique that forms a smooth connection. The smooth bend 140 is configured such that the device 100 can be recaptured in a capsule or other container after the device 100 has been at least partially deployed.

The device 100 can further include a first sealing member 162 on the valve support 110 and a second sealing member 164 on the anchoring member 120. The first and second sealing members 162, 164 can be made from a flexible material, such as Dacron® or another type of polymeric material. The first sealing member 162 can cover the interior and/or exterior surfaces of the valve support 110. In the embodiment illustrated in FIG. 6A, the first sealing member 162 is attached to the interior surface of the valve support 110, and the prosthetic valve assembly 150 is attached to the first sealing member 162 and commissure portions of the valve support 110. The second sealing member 164 is attached to the inner surface of the anchoring member 120. As a result, the outer annular engagement surface of the fixation structure 130 is not covered by the second sealing member 164 so that the outer annular engagement surface of the fixation structure 130 directly contacts the tissue of the native annulus.

The device 100 can further include an extension member 170. The extension member 170 can be an extension of the second sealing member 164, or it can be a separate component attached to the second sealing member 164 and/or the first portion 132 of the fixation structure 130. The extension member 170 can be a flexible member that, in a deployed state as shown in FIG. 6A, flexes relative to the first portion 132 of the fixation structure 130. In operation, the extension member 170 guides the device 100 during implantation such that the device is located at a desired elevation and centered relative to the native annulus. In some embodiments, one or more components of the extension member 170 can be made of or include a radiopaque material.

FIG. 7 is a top isometric view of an example of the device 100. In this embodiment, the valve support 110 defines a first frame (e.g., an inner frame) and fixation structure 130 of the anchoring member 120 defines a second frame (e.g., an outer frame) that each include a plurality of structural elements. The fixation structure 130, more specifically, includes structural elements 137 arranged in diamond-shaped cells 138 that together form at least a substantially cylindrical ring when freely and fully expanded as shown in FIG. 7. The structural elements 137 can be struts or other structural features formed from metal, polymers, or other suitable materials that can self-expand or be expanded by a balloon or other type of mechanical expander.

Several embodiments of the fixation structure 130 can be a generally cylindrical fixation ring having an outwardly facing engagement surface. For example, in the embodiment shown in FIG. 7, the outer surfaces of the structural elements 137 define an annular engagement surface configured to press outwardly against the native annulus in the deployed state. In a fully expanded state without any restrictions, the fixation structure 130 is at least substantially parallel to the valve support 110. However, the fixation structure 130 can flex inwardly (arrow I) in the deployed state when it presses radially outwardly against the inner surface of the native annulus of a heart valve.

The embodiment of the device 100 shown in FIG. 7 includes the first sealing member 162 lining the interior surface of the valve support 110, and the second sealing member 164 along the inner surface of the fixation structure 130. The extension member 170 has a flexible web 172 (e.g., a fabric) and a support member 174 (e.g., metal or polymeric strands) attached to the flexible web 172. The flexible web 172 can extend from the second sealing member 164 without a metal-to-metal connection between the fixation structure 130 and the support member 174. For example, the extension member 170 can be a continuation of the material of the second sealing member 164. Several embodiments of the extension member 170 are thus a floppy structure that can readily flex with respect to the fixation structure 130. The support member 174 can have a variety of configurations and be made from a variety of materials, such as a double-serpentine structure made from Nitinol.

FIGS. 8A-8D show one embodiment of a prosthetic heart valve device 200 ("the device 200") having an extension member 270 configured to fold or bend onto itself in the delivery configuration (FIGS. 8A and 8B) and unfurl to an extended configuration when deployed (FIGS. 8C and 8D). As such, the collapsible extension member 270 reduces the total length of the device 200 in the delivery configuration without sacrificing the lateral coverage of the extension member 270 in the deployed or extended configuration (as compared to a similar device having a non-folded extension member in the delivery configuration). The reduced length of the device 200 improves the maneuverability of the catheter C when the device 200 is positioned within the catheter lumen, which is especially beneficial when navigating the tortuous intravascular and/or intracardiac path to the mitral valve annulus. Such improved maneuverability, for example, can be particularly advantageous for making the sharp turn towards the mitral valve annulus after crossing the inter-atrial septum IAS during a trans-septal approach (discussed above with reference to FIGS. 1 and 2).

The device 200 shown in FIGS. 8A-8D can include components that are generally similar in structure and function to those of the device 100 in FIGS. 6A-7. For example, the device 200 can include the valve support 110 (not shown for ease of illustration), the anchoring member 120 (FIG. 8D only), the prosthetic valve assembly 150 (not shown for ease of illustration), and the second sealing member 164 (not shown for ease of illustration), all of which are generally similar to those discussed above with reference to FIGS. 6A-7. As such, common acts and structures and/or substructures are identified by the same reference numbers, and only significant differences in operation and structure are described below.

FIG. 8A shows a distal portion of the device 200 in a delivery configuration within a catheter C. The extension member 270 has a flexible web 272 and a support member 274 attached to the flexible web 272. In the embodiment shown in FIGS. 8A-8D, the flexible web 272 is a continuation of the material of the second sealing member 164, and the support member 274 is spaced apart from the fixation structure 130 along the second sealing member 164. In other embodiments, the flexible web 272 is not integral with the second sealing member 164 (e.g., the flexible web 272 is a separate piece of fabric), and/or the support member 274 is integral with the fixation structure 130. Moreover, although the embodiment shown in FIG. 8A shows the support member 274 disposed at an interior region of the flexible web 272 (e.g., between two layers of fabric), in other embodiments the support member 274 may be positioned at a surface of the web 272. For example, in some embodiments the support member 274 may be positioned on an atrial surface 272a (see FIG. 8D) of the web 272, and in other embodiments the support member 274 may be positioned on a ventricular surface 272b (see FIG. 8D) of the web 272.

FIG. 8B is an enlarged, isolated view of a portion of the extension member 270 and fixation structure 130 shown in FIG. 8A. Referring to FIGS. 8A and 8B together, the extension member 270 has a longitudinal axis LE, a first terminus 287 at the fixation structure 130, a free second terminus 288, and a length measured along the longitudinal axis LE (FIG. 8B) between the first and second termini 287, 288. The extension member 270 also has a first portion 282 and a second portion 284 extending along its longitudinal axis LE (FIG. 8B). The first portion 282 meets or is otherwise coupled to the second portion 284 at a joint 286. The first portion 282 has a length measured between the first terminus 287 of the extension member 270 and the joint 286, and the second portion 284 has a length measured between the joint 286 and the second terminus 288 of the extension member 270. The support member 274 extends along the longitudinal axis LE from a first location along the first portion 282 to a second location along the second portion 284. As discussed in greater detail below, the support member 274 is configured to preferentially bend at the joint 286 of the extension member 270. In certain embodiments, the support member 274 extends only a portion of the length of the extension member 270, and in some embodiments the support member 274 extends the entire length of the extension member 270. The support member 274 can have a variety of configurations and be made from a variety of materials.

When positioned in the delivery configuration within the catheter C (e.g., FIG. 8A), the extension member 270 may be folded back on itself such that at least a portion of the first portion 282 overlaps at least a portion of the second portion 284 and the extension member 270 includes a folded or bent edge at the joint 286. For example, in the embodiment shown in FIG. 8A, the first portion 282 extends distally from the fixation structure 130 and/or first terminus 287 to the joint 286, and the second portion 284 extends proximally from the joint 286 to the second terminus 288. As shown, the extension member 270 may be folded or configured to fold at a single location along the longitudinal axis of the support member 274 and/or extension member 270, thereby dividing the extension member 270 into the first and second portions 282, 284. In other embodiments, the extension member 270 may be folded and/or configured to fold or bend at multiple locations along the longitudinal axis of the support member 274 and/or extension member 270 (e.g., like an accordion), thereby dividing the extension member 270 into more than two portions. Although the second portion 284 is shown positioned radially inward of the first portion 282 in FIGS. 8A and 8B, in other embodiments the second portion 284 can be positioned radially outward of the first portion 282 in the delivery configuration.

In the embodiment shown in FIGS. 8A and 8B, the length of the first portion 282 is greater than the length of the second portion 284 such that the free second terminus 288 is distal of the first terminus 287 along the longitudinal axis Lo (FIG. 8A) of the device 200 when the device 200 is in the delivery configuration. In other embodiments, the length of the first portion 282 is substantially the same as the length of the second portion 284 such that the free second terminus 288 is adjacent or aligned with the first terminus 287 along the longitudinal axis Lo of the device 200 when the device 200 is in the delivery configuration. In yet other embodiments, the length of the first portion 282 can be less than the length of the second portion 284 such that the second terminus 288 is proximal of the first terminus 287 along the longitudinal axis Lo of the device 200 when the device 200 is in the delivery configuration.

FIG. 8C is a cross-sectional view of the extension member 270 as it releases from a distal end of the delivery catheter C and transforms from the delivery configuration to a deployed or extended configuration. FIG. 8D is a cross-sectional, isolated view of the anchoring member 120, second sealing member 164, and extension member 270 when the device 200 is in a deployed configuration. Referring to FIGS. 8C and 8D together, as the extension member 270 releases from the distal end of the delivery catheter C, the first portion 282 rotates radially away from a central longitudinal axis Lo of the device 200 (indicated by arrows A1 in FIG. 8C) around the first terminus 287, while the second portion 284 rotates radially away from the longitudinal axis Lo around the joint 286 (indicated by arrows A2 in FIG. 8C) until the longitudinal axis's of the first and second portions 282, 284 are generally aligned (e.g., the first and second portions 282, 284 are generally within the same plane along their lengths) unless otherwise constrained by the anatomy. As such, in the deployed configuration, the first portion 282 extends radially outwardly from the fixation structure 130, and the second portion 284 extends radially outwardly from the first portion 282. In other embodiments, the extension member 270 may be configured such that the second portion 284 is positioned at an angle with respect to the first portion 282 when the device 200 is in the deployed configuration. In any of the above embodiments, the distance between the first terminus 287 and the second terminus 288 of the extension member 270 is less when the extension member 270 is in the delivery configuration than when the extension member 270 is in the deployed configuration, thereby improving the maneuverability of the delivery system without sacrificing the lateral coverage of the extension member 270 in the deployed or extended configuration.

FIGS. 9A-9C show another embodiment of a prosthetic heart valve device 300 ("the device 300") having an extension member 370 configured to fold or bend onto itself in the deployed configuration (FIG. 9C). The device 300 shown in FIGS. 9A-9C can include components that are generally similar in structure and function to those of the device 100 in FIGS. 6A-7. For example, the device 300 can include the valve support 110 (not shown for ease of illustration), the anchoring member 120 (FIG. 9C only), the prosthetic valve assembly 150 (not shown for ease of illustration), and the second sealing member 164 (not shown for ease of illustration), all of which are generally similar to those discussed above with reference to FIGS. 6A-7. As such, common acts and structures and/or sub-structures are identified by the same reference numbers, and only significant differences in operation and structure are described below.

FIG. 9A shows a distal portion of the device 300 in a delivery configuration within a catheter C. The extension member 370 has a flexible web 372 and a support member 374 attached to the flexible web 372. In the embodiment shown in FIGS. 9A-9C, the flexible web 372 is a continuation of the material of the second sealing member 164, and the support member 374 is spaced apart from the fixation structure 130 along the second sealing member 164. In other embodiments, the flexible web 372 is not integral with the second sealing member 164 (e.g., the flexible web 372 is a separate piece of material), and/or the support member 374 is integral with the fixation structure 130. Moreover, although the embodiment shown in FIG. 9A shows the support member 374 disposed at an interior region of the flexible web 372 (e.g., between two layers of fabric), in other embodiments the support member 374 may be positioned at a surface of the web 372.

As shown in FIG. 9A, the extension member 370 has a first terminus 387 at the fixation structure 130, a free second terminus 388, and a length measured along its longitudinal axis LE between the first and second termini 387, 388. The extension member 370 also has a first portion 382 and a second portion 384 extending along its longitudinal axis LE. The first portion 382 meets or is otherwise coupled to the second portion 384 at a joint 386. The first portion 382 has a length measured between the first terminus 387 of the extension member 370 and the joint 386, and the second portion 384 has a length measured between the joint 386 and the second terminus 388 of the extension member 370. The support member 374 extends along the longitudinal axis LE of the extension member 370 from a first location along the first portion 382 to a second location along the second portion 384, and the support member 374 is configured to preferentially bend at the joint 386 of the extension member 370, as discussed in greater detail below. In certain embodiments the support member 374 extends only a portion of the length of the extension member 370, but in other embodiments the support member 374 extends the entire length of the extension member 370. The support member 374 can have a variety of configurations and be made from a variety of materials.

As shown in FIG. 9A, in the delivery configuration, the extension member 370 can be generally straight such that the first portion 382 extends distally from the fixation structure 130, and the second portion 384 extends distally from the joint 386. As such, the free second terminus 388 is spaced apart from the first terminus 387 by a distance measured along a longitudinal axis LE of the extension member 370 that is at least the combined lengths of the first portion 382 and the second portion 384. Advantageously, the joint 386 of extension member 370 provides an articulation and/or flexing point that improves the flexibility of the distal portion of the delivery system (i.e., delivery catheter C and device 300 loaded therein), at least as compared to an extension member that does not include a joint along its length. As such, the joint 386 improves the maneuverability of the catheter C when the device 200 is positioned within the catheter lumen, which is especially beneficial when navigating the tortuous intravascular and/or intracardiac path to the mitral valve annulus, as discussed above with reference to FIGS. 8A-D. The joint 386 additionally improves the flexibility of the extension member 370 when the device 300 is positioned at the annulus, thereby allowing the device 300 to better adapt and conform to the local anatomy.

FIG. 9B is a cross-sectional view of the extension member 370 as it releases from a distal end of the delivery catheter C and transforms from the delivery configuration to a deployed or folded configuration, and FIG. 9C is a cross-sectional, isolated view of the anchoring member 120, second sealing member 164, and extension member 370 when the device 300 is in a deployed configuration. Referring to FIGS. 9B and 9C together, when the extension member 370 is released from a distal end of the delivery catheter C, the extension member 370 folds back on itself such that the first portion 382 rotates radially away from the central longitudinal axis Lo of the device 300 (indicated by arrows A1 in FIG. 9B) about the first terminus 387, and the second portion 384 rotates radially toward the central longitudinal axis Lo (indicated by arrows A3 in FIG. 9B) about the joint 386. As such, in the deployed configuration, at least a portion of the second portion 384 overlaps at least a portion of the first portion 382 and the joint 386 therebetween forms a folded or bent edge.

In the illustrated embodiment, the second portion 384 rotates towards the fixation structure 130 in an upstream direction (indicated by arrows A3 in FIG. 9B) such that the second portion 384 is positioned upstream of the first portion 382 in the expanded configuration. In other embodiments, such as the device 300' shown in FIGS. 10A-10C, the second portion 384 rotates towards the fixation structure 130 in a downstream direction (indicated by arrows A4 in FIG. 10B) such that the second portion 384 is positioned downstream of the first portion 382 in the expanded configuration. Moreover, in the embodiment shown in FIGS. 9B and 9C, the extension member 370 is folded or configured to fold at a single location along the longitudinal axis of the support member 374, thereby dividing the extension member 370 into the first and second portions 382, 384. In other embodiments, the extension member 370 may be folded and/or configured to fold or bend at multiple locations along the longitudinal axis of the support member 374 (e.g., like an accordion), thereby dividing the extension member 370 into more than two portions.

In any of the embodiments disclosed herein, the length of the first portion 382 is substantially the same as the length of the second portion 384 such that the second free terminus 388 is adjacent or aligned with the first terminus 387 along a line L (FIG. 9C) substantially parallel to the longitudinal axis of the first portion 382 when the device 300 is expanded. In such embodiments, the distance between the second terminus 388 and the first terminus 387 along the line L is substantially zero. In other embodiments, the length of the first portion 382 can be greater than the length of the second portion 384 such that the second terminus 388 is radially outward of and spaced apart from the first terminus 387 along the line L when the device 300 is expanded. In yet other embodiments, the length of the first portion 382 can be less than the length of the second portion 384 such that the second terminus 388 is radially inward of and spaced apart from the first terminus 387 along the line L when the device 300 is expanded.

In any of the foregoing embodiments, the extension member may include one or more impedance sensors for detecting or otherwise assessing contact between the extension member and adjacent tissue (e.g., the leaflets, the atrial floor, etc.) while the prosthetic heart valve device is being positioned within the mitral annulus. For example, in some embodiments the support member may be formed of a metal wire coated or otherwise surrounded by an insulative material. The support member can include one or more impedance sensors comprising portions of the metal wire exposed through corresponding openings in the insulative material. The wire may be electrically coupled to a conductive member that extends proximally from the prosthetic heart valve device to a proximal portion (e.g., a handle) of the delivery system. For example, in some embodiments the metal wire may be directly coupled to the conductive member (i.e., in direct contact), and in other embodiments the metal wire may be indirectly coupled to the conductive member via the anchoring member and/or another conductive component of the device.

Examples

The following examples are illustrative of several embodiments of the present technology:

1. A prosthetic heart valve device comprising:
   an anchoring member having an annular fixation structure with an upstream portion and a downstream portion;
   a tubular valve support having a first portion coupled to the upstream portion of the anchoring member and a second portion spaced radially inward from the upstream portion of the anchoring member;
   a valve assembly coupled to the valve support and having at least one leaflet movable from a closed position in which blood flow is blocked through the valve support and an open position in which blood flow is allowed through the valve support in a downstream direction; and
   an extension member having an annular first portion coupled to the fixation structure and a second portion coupled to the first portion, wherein—
   the extension member folds back on itself in a delivery configuration such that the first portion extends distally from the fixation structure and the second portion extends back proximally from the first portion, and
   when the extension member is in a deployed configuration, the first portion extends radially outwardly from the fixation structure and the second portion extends radially outwardly from the first portion.

2. The device of example 1 wherein the second portion is positioned radially inwardly of the first portion in the delivery configuration.

3. The device of example 1 wherein the second portion is positioned radially outwardly of the first portion in the delivery configuration.

4. The device of any one of examples 1-3 wherein the extension member has a first terminus at the anchoring member and a free second terminus, wherein a length of the first portion is substantially the same as a length of the second portion such that, when the device is in the delivery configuration, the free second terminus is axially aligned with the first terminus along a line substantially parallel to the longitudinal axis of the device.

5. The device of any one of examples 1-3 wherein the extension member has a first terminus at the anchoring member and a free second terminus, and wherein a length of the first portion is greater than a length of the second portion such that, when the device is in the delivery configuration, the second terminus is distal of the first terminus along a line substantially parallel to the longitudinal axis of the device.

6. The device of any one of examples 1-3 wherein the extension member has a first terminus at the anchoring member and a free second terminus, and wherein a length of the first portion is less than a length of the second portion such that, when the device is in the delivery configuration, the second terminus is proximal of a first terminus along a line substantially parallel to the longitudinal axis of the device.

7. The device of any one of examples 1-6 wherein, in the expanded configuration, the first portion and the second portion have a straight configuration such that the first portion is not at an angle with respect to the second portion.

8. The device of any one of examples 1-7 wherein the extension member includes one or more impedance sensors.

9. A prosthetic heart valve device comprising:
an anchoring member having a radially expandable frame with an interior and having an upstream portion and a downstream portion, wherein the upstream portion includes a tissue fixation portion configured to press outwardly against tissue located at and/or downstream of a native annulus of a heart valve in a subject and configured to be at least partially deformable to conform to a shape of the tissue;
a valve positioned relative to the anchoring member and having at least one leaflet movable from a closed position in which blood flow is blocked through the interior and an open position in which blood flow is allowed through the interior in a flow direction from the upstream portion toward the downstream portion, wherein the valve is spaced inwardly apart from the tissue fixation portion of the anchoring member such that the valve remains competent when the tissue fixation portion is deformed to conform to the shape of the tissue; and
an extension member having a first terminus at the anchoring member and a second, free terminus, wherein—
the extension member has a delivery configuration in which the extension member extends distally from the anchoring member, has an inverted distal portion, and the second, free terminus is spaced apart from the first terminus by a first distance, and
the extension member has a deployed configuration in which the extension member extends laterally away from the anchoring member such that the second, free terminus is spaced apart from the first terminus by a second distance greater than the first distance.

10. The device of example 9 wherein the second free terminus is distal of the first terminus when the extension member is in the delivery configuration.

11. The device of example 9 wherein the second free terminus is proximal of the first terminus when the extension member is in the delivery configuration.

12. The device of any one of examples 9-11 wherein the extension member includes a flexible web and a support member extending along at least a portion of the length of the extension member, the support member attached to the web.

13. The device of any one of examples 9-11 wherein the extension member includes a flexible web and a superelastic material attached to the web.

14. The device of any one of examples 9-13 wherein the extension member has joint, a first portion extending between the first terminus and the joint, and a second portion extending between the joint and the second terminus, and wherein at least a portion of the first portion overlaps at least a portion of the second portion when the extension member is in a delivery configuration.

15. The device of any one of examples 9-14 wherein the extension member includes one or more impedance sensors.

16. A method for deploying a prosthetic heart valve device, the method comprising:
positioning a distal portion of a delivery catheter at a native heart annulus;
delivering a prosthetic heart valve device to the distal portion of the delivery catheter, the prosthetic heart valve device having a brim configured to be positioned at an upstream side of the annulus when the device is deployed, and wherein the brim is folded into a first portion and an overlapping second portion during delivery; and withdrawing the delivery catheter proximally thereby allowing the brim to unfold such that the brim extends laterally away from a central longitudinal axis of the prosthetic heart valve device.

17. The method of example 16 wherein withdrawing the delivery catheter proximally allows the brim to unfold such that (a) a distal end of the first portion moves radially away from the central longitudinal axis of the device, and (b) a distal end of the second portion moves radially towards the central longitudinal axis of the device.

18. The method of example 16 wherein—
the brim includes a joint and the first portion and the second portion are coupled at the joint, and wherein a proximal terminus of the first portion is coupled to an upstream region of an anchoring member of the device; and
withdrawing the delivery catheter proximally allows the brim to unfold such that (a) the first portion rotates away from the central longitudinal axis of the device about the proximal terminus, and (b) the second portion rotates radially away from the central longitudinal axis of the device about the joint.

19. A prosthetic heart valve device comprising:
an anchoring member having an annular fixation structure with an upstream portion and a downstream portion;
a tubular valve support having a first portion coupled to the upstream portion of the anchoring member and a second portion spaced radially inward from the upstream portion of the anchoring member;
a valve assembly coupled to the valve support and having at least one leaflet movable from a closed position in which blood flow is blocked through the valve support and an open position in which blood flow is allowed through the valve support in a downstream direction; and
an extension member having an annular first portion coupled to the fixation structure and a second portion coupled to the first portion, wherein—
the extension member is generally linear in a delivery configuration such that the first portion extends distally from the fixation structure and the second portion extends distally from the first portion, and
the extension member folds back on itself in a deployed configuration such that the first portion extends radially outwardly from the fixation structure and the second portion extends back towards the fixation structure.

20. The device of example 19 wherein the second portion extends back towards the fixation structure in an upstream direction such that the second portion is positioned upstream of the first portion in the deployed configuration.

21. The device of example 18 wherein the second portion extends back towards the fixation structure in a downstream direction such that the second portion is positioned downstream of the first portion in the deployed configuration.

22. The device of any one of examples 19-21 wherein the extension member has a first terminus at the anchoring member and a free second terminus, wherein a length of the first portion is substantially the same as a length of the second portion such that, when the device is expanded, the second terminus is axially aligned with the first terminus along a line substantially parallel to the longitudinal axis of the first portion.

23. The device of any one of examples 19-21 wherein the extension member has a first terminus at the anchoring member and a free second terminus, and wherein a length of the first portion is greater than a length of the second portion such that, when the device is expanded, the second terminus is radially outward of and spaced apart from the first terminus along a line substantially parallel to the longitudinal axis of the first portion.

24. The device of any one of examples 19-21 wherein the extension member has a first terminus at the anchoring member and a free second terminus, and wherein a length of the first portion is less than a length of the second portion such that, when the device is expanded, the second terminus is radially inward of and spaced apart from the first terminus along a line substantially parallel to the longitudinal axis of the first portion.

25. The device of any one of examples 19-24 wherein, in the expanded configuration, the first portion and the second portion have a straight configuration such that the first portion is not at an angle with respect to the second portion.

26. A prosthetic heart valve device comprising:
  an anchoring member having a radially expandable frame with an interior and having an upstream portion and a downstream portion, wherein the upstream portion includes a tissue fixation portion configured to press outwardly against tissue located at and/or downstream of a native annulus of a heart valve in a subject and configured to be at least partially deformable to conform to a shape of the tissue;
  a valve positioned relative to the anchoring member and having at least one leaflet movable from a closed position in which blood flow is blocked through the interior and an open position in which blood flow is allowed through the interior in a flow direction from the upstream portion toward the downstream portion, wherein the valve is spaced inwardly apart from the tissue fixation portion of the anchoring member such that the valve remains competent when the tissue fixation portion is deformed to conform to the shape of the tissue; and
  an extension member having a first terminus at the anchoring member and a second, free terminus, wherein—
    the extension member has a delivery configuration in which the extension member extends in a generally straight configuration and the second, free terminus is spaced apart from the first terminus by a first distance, and
    wherein the extension member has a deployed configuration in which the extension member extends laterally away from the anchoring member, has an inverted distal portion, and the second, free terminus is spaced apart from the first terminus by a second distance less than the first distance.

27. The device of example 26 wherein the extension member includes a flexible web and a support member extending along at least a portion of the length of the extension member, the support member attached to the web.

28. A method for deploying a prosthetic heart valve device, the method comprising:
  positioning a distal portion of a delivery catheter at a native heart annulus;
  delivering a prosthetic heart valve device to the distal portion of the delivery catheter, the prosthetic heart valve device having a brim configured to be positioned at an upstream side of the annulus when the device is deployed, and wherein the brim has a first portion and a second portion positioned distal to the first portion during delivery; and
  withdrawing the delivery catheter proximally thereby allowing the brim to fold back on itself such that (a) a distal end of the first portion moves in a first direction relative to a central longitudinal axis of the deployed device, and (b) a distal end of the second portion moves in a second direction relative to the central longitudinal axis that is opposite the first direction.

29. The method of example 28 wherein withdrawing the delivery catheter proximally allows the brim to fold back on itself such that (a) a distal end of the first portion moves away from the central longitudinal axis of the deployed device, and (b) a distal end of the second portion moves toward the central longitudinal axis.

30. The method of example 29 wherein withdrawing the delivery catheter proximally allows the brim to fold back on itself such that (a) a distal end of the first portion moves toward the central longitudinal axis of the deployed device, and (b) a distal end of the second portion moves away from the central longitudinal axis.

From the foregoing, it will be appreciated that specific embodiments of the invention have been described herein for purposes of illustration, but that various modifications may be made without deviating from the scope of the invention. For example, several individual components can be interchange with each other in the different embodiments. Accordingly, the invention is not limited except as by the appended claims.

We claim:

1. A method for deploying a prosthetic heart valve device, the method comprising:
  positioning a distal portion of a delivery catheter at a native heart annulus, wherein the distal portion of the delivery catheter includes a prosthetic heart valve device, the prosthetic heart valve device having an extension member, wherein the extension member includes an annular first portion having a first end coupled to and extending from a portion of the prosthetic heart valve device and a second portion including a first end coupled to a second end of the first portion at a joint, wherein during delivery with at least a second end of the second portion opposite the first end of the second portion disposed within the distal portion of the delivery catheter, the second portion is folded back towards the first portion; and
  withdrawing the delivery catheter proximally thereby allowing the extension member to unfold such that the extension member extends laterally away from a central longitudinal axis of the prosthetic heart valve device and such that longitudinal axes of the first portion and the second portion are substantially aligned.

2. The method of claim 1,
  wherein when withdrawing the delivery catheter proximally (a) the second end of the first portion moves radially away from the central longitudinal axis of the device, and (b) the second end of the second portion moves radially towards the central longitudinal axis of the device.

3. The method of claim 1 wherein:
  the first end of the first portion is coupled to an upstream region of an anchoring member of the device; and
  withdrawing the delivery catheter proximally allows the extension member to unfold such that (a) the first portion rotates away from the central longitudinal axis of the device about the proximal end, and (b) the second portion rotates radially away from the central longitudinal axis of the device about the joint.

4. The method of claim 1,
wherein in a delivery configuration, the extension member is folded back on itself at the joint such that the first portion extends distally from a fixation structure of the prosthetic heart valve and the second portion extends back proximally from the first portion and is substantially parallel to the first portion, and
wherein the extension member unfolds into a deployed configuration in which the first portion extends radially outwardly from the fixation structure and the second portion extends radially outwardly from the first portion.

5. The method of claim 1, wherein the prosthetic heart valve device comprises a valve support including a prosthetic valve coupled thereto and an anchoring member surrounding at least a portion of the valve support, wherein the extension member is coupled to the anchoring member.

6. The method of claim 5, wherein the extension member extends proximally from an inflow end of the anchoring member.

7. The method of claim 1, wherein the anchoring member includes a fixation structure and a sealing member coupled to the fixation structure, wherein the extension member is coupled to the sealing member.

8. The method of claim 7, wherein the extension member is an extension of the sealing member.

9. A method for deploying a prosthetic heart valve device, the method comprising:
positioning a distal portion of a delivery catheter at a native heart annulus, wherein the distal portion of the delivery catheter includes a prosthetic heart valve device, the prosthetic heart valve device having an extension member wherein the extension member has a first portion having a first end coupled to and extending from an inflow region of the prosthetic heart valve device and a second portion including a first end coupled to a second end of the first portion at a joint, wherein in a delivery configuration, the extension member is configured to be generally linear such that the first portion extends distally from a fixation structure of the prosthetic heart valve and the second portion extends from the first portion, wherein in the delivery configuration, the first portion includes a first portion outer surface and a first portion inner surface and the second portion includes a second portion outer surface and a second portion inner surface; and
withdrawing the delivery catheter from the prosthetic heart valve device, thereby allowing the extension member to fold back on itself at the joint into a deployed configuration such that the first portion extends radially outwardly from the fixation structure and the second portion extends back towards the fixation structure, the second portion is substantially parallel to the first portion, and the second portion outer surface abuts the first portion outer surface.

10. The method of claim 9, wherein withdrawing the delivery catheter proximally thereby allowing the extension member to fold back on itself such that (a) the distal end of the first portion moves away from the central longitudinal axis of the prosthetic heart valve device, and (b) the second end of the second portion moves away from the central longitudinal axis.

11. A method for deploying a prosthetic heart valve device, the method comprising:
positioning a distal portion of a delivery catheter at a native heart annulus, wherein the distal portion of the delivery catheter includes a prosthetic heart valve device, the prosthetic heart valve device having an extension member wherein the extension member has a first portion having a first end coupled to and extending from an inflow region of the prosthetic heart valve device and a second portion including a first end coupled to a second end of the first portion at a joint, wherein in a delivery configuration, the extension member is configured to be generally linear such that the first portion extends from a fixation structure of the prosthetic heart valve device and the second portion extends from the first portion along a common longitudinal axis; and
withdrawing the delivery catheter from the prosthetic heart valve device, thereby allowing the extension member to fold back on itself such that (a) the second end of the first portion rotates away from the central longitudinal axis of the prosthetic heart valve device, and (b) the second end of the second portion rotates inwardly and in an upstream direction toward the central longitudinal axis.

\* \* \* \* \*